(12) United States Patent
Bales, Jr. et al.

(10) Patent No.: US 9,737,354 B2
(45) Date of Patent: Aug. 22, 2017

(54) BATTERY-POWERED ELECTROSURGICAL FORCEPS WITH MULTI-TURN SELECTABLE-RATIO TRANSFORMER

(71) Applicant: Syntheon, LLC, Miami, FL (US)

(72) Inventors: Thomas O. Bales, Jr., Miami, FL (US); Matthew A. Palmer, Miami, FL (US); Kevin W. Smith, Coral Gables, FL (US)

(73) Assignee: Syntheon, LLC, Miami, FL (US)

( * ) Notice: Subject to any disclaimer, the term of this patent is extended or adjusted under 35 U.S.C. 154(b) by 77 days.

(21) Appl. No.: 14/844,473

(22) Filed: Sep. 3, 2015

(65) Prior Publication Data

US 2016/0022348 A1 Jan. 28, 2016

Related U.S. Application Data

(62) Division of application No. 13/004,670, filed on Jan. 11, 2011, now Pat. No. 9,155,585.

(Continued)

(51) Int. Cl.
*A61B 18/12* (2006.01)
*A61B 18/14* (2006.01)
(Continued)

(52) U.S. Cl.
CPC ...... *A61B 18/1206* (2013.01); *A61B 18/1442* (2013.01); *H01F 27/28* (2013.01);
(Continued)

(58) Field of Classification Search
CPC ............ A61B 18/1442; A61B 18/1206; A61B 2018/1226; A61B 2018/1286; H01F 27/40; H01F 27/28
(Continued)

(56) References Cited

U.S. PATENT DOCUMENTS 5,602,462 A * 2/1997 Stich .................. G05F 1/147
307/64
5,825,164 A 10/1998 Williams
(Continued)

FOREIGN PATENT DOCUMENTS

| EP | 0137347 | 4/1985 |
|---|---|---|
| EP | 1071199 | 1/2001 |
| EP | 1751863 | 8/2009 |

OTHER PUBLICATIONS

International Search Report and Written Opinion for International Application No. PCT/US2011/020914 dated Mar. 14, 2011.

*Primary Examiner* — Thomas Giuliani
(74) *Attorney, Agent, or Firm* — Mayback & Hoffman, P.A.; Gregory L. Mayback; Rebecca A Tie (57) ABSTRACT

An electrocautery surgical device comprising a battery source and radio-frequency signal generating circuitry electrically coupled to the battery source and operable to deliver power. In an exemplary embodiment, the radio-frequency signal generating circuitry comprises a transformer having a primary winding and a secondary winding wherein the secondary winding is comprised of a first secondary sub-winding and a second secondary sub-winding, at least one switching component electrically coupled to the first and second secondary sub-windings and operable to switch between engaging the first secondary sub-winding and engaging the second secondary sub-winding such that a current induced by the primary winding flows through either the first secondary sub-winding or the second secondary sub-winding, wherein the first and second secondary sub-windings have a different number of turns such that the radio-frequency signal generating circuitry produces a different impedance value depending on which of the first or second secondary sub-windings is engaged.

9 Claims, 9 Drawing Sheets

Related U.S. Application Data (60) Provisional application No. 61/294,152, filed on Jan. 12, 2010.

(51) Int. Cl.
*H01F 27/28* (2006.01)
*H01F 27/40* (2006.01)

(52) U.S. Cl.
CPC ...... *H01F 27/40* (2013.01); *A61B 2018/1226* (2013.01); *A61B 2018/1286* (2013.01)

(58) Field of Classification Search
USPC .......... 606/34, 37–40, 42, 45, 46, 48, 50–52
See application file for complete search history.

(56) References Cited

U.S. PATENT DOCUMENTS

| | | | | |
|---|---|---|---|---|
| 6,317,336 | B1 * | 11/2001 | Jiang | H02M 3/33569 323/255 |
| 7,427,887 | B2 | 9/2008 | O'Donnell et al. | |
| 9,155,585 | B2 * | 10/2015 | Bales, Jr. | A61B 18/1206 |
| 2001/0048356 | A1 | 12/2001 | Owen | |
| 2003/0048165 | A1 | 3/2003 | Rapoport et al. | |
| 2003/0102774 | A1 | 6/2003 | Carazo et al. | |
| 2006/0018135 | A1 * | 1/2006 | Yang | H02M 3/33592 363/21.14 |
| 2008/0154255 | A1 | 6/2008 | Panos et al. | |
| 2009/0240246 | A1 | 9/2009 | Deville et al. | |

\* cited by examiner

BATTERY-POWERED ELECTROSURGICAL FORCEPS WITH MULTI-TURN SELECTABLE-RATIO TRANSFORMER

CROSS-REFERENCE TO RELATED APPLICATIONS

The present application is a divisional application of U.S. patent application Ser. No. 13/004,670, filed on Jan. 11, 2011, now U.S. Pat. No. 9,155,585, issued on Oct. 13, 2015, which claims priority, under 35 U.S.C. §119, of U.S. Provisional Patent Application Serial No. 61/294,152, filed on Jan. 12, 2010, the entire disclosures of which are hereby incorporated herein by reference in their entireties.

FIELD OF INVENTION

The present invention lies in the field of medical cauterization and cutting devices. The present disclosure relates to a method for powering a cordless electrosurgical forceps for sealing and/or cutting tissue.

BACKGROUND OF THE INVENTION

Electrosurgical forceps utilize both mechanical clamping action and electrical energy to effect hemostasis by heating the tissue and blood vessels to coagulate, cauterize and/or seal the tissue. As an alternative to open forceps for use with open surgical procedures, many modern surgeons use endoscopes, laparoscopes, and endoscopic/laparoscopic instruments for remotely accessing organs through body orifices or smaller, puncture-like incisions. As a direct result thereof, patients tend to benefit from less scarring and reduced healing time.

Laparoscopic instruments are inserted into the patient through a cannula, or port, which has been made with a trocar. Typical sizes for cannulas range from three millimeters to twelve millimeters. Smaller cannulas are usually preferred, which, as can be appreciated, ultimately presents a design challenge to instrument manufacturers who must find ways to make laparoscopic instruments that fit through the smaller cannulas. Prior art RF vessel sealing devices require a table-top power-and-signal supply box connected to the electrodes of the jaws through a cumbersome power-and-signal supply line. The supply box takes up precious room within an operating suite. In addition, the supply box is expensive to produce, requiring the surgeon/hospital to expend significant amounts of capital to keep the unit on hand. Additionally, the supply line adds cost to produce and maintain. Importantly, the supply line commonly interferes with the surgeon's full freedom of movement during use.

Recently, the inventors have developed state of the art electrosurgical devices, such as RF bipolar vessel sealers and ultrasonic scalpel/vessel sealers, which allow all of the components to be contained in a single hand-held device, thus alleviating the heavy and expensive countertop box. This development is due, in part, to the creative use of small and light-weight but powerful battery packs that have, for example, transformed the hand-held commercial and consumer power tool markets over the past several years. This technology has already found its way into the operating room in the form of orthopedic drills, saws, and screwdrivers. However, batteries applied to cautery power supplies provide unique technical hurdles due to the limitations of their power-delivery characteristics.

For example, as current flows through a battery pack, its voltage drops due to its inherent internal impedance. This limits its capability to deliver maximum power. If the load to which the battery is connected differs in impedance greatly from its internal impedance, the battery cannot deliver its full power potential. This limitation cripples the ability of the battery pack to compete with a mains-powered box as a viable alternative.

Present lithium-ion battery packs are capable of delivering power in the 200 W range, which is ample power to perform a satisfactory vessel seal. However, due to an increase in the impedance of the tissue during desiccation, the battery cannot deliver this level of power throughout the entire sealing process. More specifically, the impedance of biologic tissue is in the 3-Ohm range. Desiccated tissue can develop an impedance as high as about 100 Ohms. Because the internal impedance of a typical Li-ion battery pack is only about 0.8 Ohms, a battery feeding a fixed-turns-ratio transformer cannot be made to accommodate the very wide impedance range and deliver power to its potential during an operation. If the impedance of the load could be made to more closely match the impedance of the battery, then the battery would be able to provide the necessary power.

Thus, a need exists to overcome the problematic issues discussed above.

SUMMARY OF THE INVENTION

Briefly, embodiments of the present invention provide a multiple-tap primary transformer in a battery-powered electrocautery generator. By utilizing multiple MOSFET-pair drivers connected to a single, multi-tapped primary, instant changing of impedance is available. Advantageously, all switching takes place at primary voltage, thereby allowing efficient use of low-impedance batteries with loads of different or varying load impedances. Impedance switching is effectively instantaneous, so that, in an arc-producing application, the arc may be maintained without interruption (as would be required with relay-switching).

In other embodiments, the integrated DC-DC converter chips may be replaced by discrete devices or by circuits with lower levels of integration, such as external switching MOSFETs. Additionally, while the above description relates to driving a high-impedance load with a low-impedance battery, batteries of any impedance can be used to drive loads of any impedance through the appropriate choice of transformer ratios.

Other features that are considered as characteristic for the invention are set forth in the appended claims.

With the foregoing and other objects in view, there is provided, in accordance with the invention, an electrocautery surgical device including a battery power source and radio-frequency signal generating circuitry electrically coupled to the battery power source and operable to deliver power to an electrosurgical forceps. The radio-frequency signal generating circuitry comprises a transformer having a primary winding and a secondary winding, the primary winding being comprised of a first primary sub-winding and a second primary sub-winding, at least one switching component electrically coupled to the first and second primary sub-windings and operable to switch between engaging the first primary sub-winding and engaging the second primary sub-winding such that a current flows through either the first primary sub-winding or the second primary sub-winding or both, and the first and second primary sub-windings having a different number of turns such that the radio-frequency signal generating circuitry produces a different impedance value depending on which one or both of the first and second primary sub-windings is engaged.

With the objects of the invention in view, there is also provided an electrocautery surgical device comprises a battery power source and radio-frequency signal generating circuitry electrically coupled to the battery power source and operable to deliver power to an electrosurgical forceps. The radio-frequency signal generating circuitry comprises a transformer having a primary winding and a secondary winding, the secondary winding being comprised of a first secondary sub-winding and a second secondary sub-winding, at least one switching component electrically coupled to the first and second secondary sub-windings and operable to switch between engaging the first secondary sub-winding and engaging the second secondary sub-winding such that a current induced by the primary winding flows through either the first secondary sub-winding or the second secondary sub-winding, and the first and second secondary sub-windings having a different number of turns such that the radio-frequency signal generating circuitry produces a different impedance value depending on which of the first or second secondary sub-windings is engaged.

With the objects of the invention in view, there is also provided an electrocautery surgical device comprises a battery power source and radio-frequency signal generating circuitry electrically coupled to the battery power source and operable to deliver power to an electrosurgical forceps. The radio-frequency signal generating circuitry comprises a transformer having a primary winding and a secondary winding, the primary winding being comprised of a first primary sub-winding and a second primary sub-winding, the first and second primary sub-windings being connected to ground, a first switching component, a second switching component, and a third switching component being electrically coupled to the first and second primary sub-windings and operable to switch between engaging the first primary sub-winding and engaging the second primary sub-winding such that a current flows through either the first primary sub-winding or the second primary sub-winding, the third switching component being connected to the second switching component and ground, and the first and second primary sub-windings having a different number of turns such that the radio-frequency signal generating circuitry produces a different impedance value depending on which of the first or second primary sub-windings is engaged.

In accordance with another feature of the invention, the primary winding has turns and is tapped at an intermediate point along the turns to create the first primary sub-winding and the second primary sub-winding.

In accordance with a further feature of the invention, the secondary winding has turns and is tapped at an intermediate point along the turns to create the first secondary sub-winding and the second secondary sub-winding.

In accordance with an added feature of the invention, the first primary sub-winding and the second primary sub-winding are separate windings electrically coupled to one another.

In accordance with an additional feature of the invention, the second primary sub-winding has a given number of turns and the first primary sub-winding has a number of turns greater than the given number of turns of the second primary sub-winding.

In accordance with yet another feature of the invention, the second secondary sub-winding has a given number of turns and the first secondary sub-winding has a number of turns greater than the given number of turns of the second secondary sub-winding.

In accordance with yet a further feature of the invention, the first primary sub-winding has a given turns ratio and the second primary sub-winding has a turns ratio greater than the given turns ratio of the first primary sub-winding.

In accordance with yet an added feature of the invention, the first secondary sub-winding has a given turns ratio and the second secondary sub-winding has a turns ratio higher than the given turns ratio of the first secondary sub-winding.

In accordance with yet an additional feature of the invention, the at least one switching component is comprised of a first MOSFET, a second MOSFET, a third MOSFET, and a fourth MOSFET, the first and second MOSFETs are electrically coupled to the second primary sub-winding, and the third and fourth MOSFETs are electrically coupled to the first primary sub-winding.

In accordance with again another feature of the invention, there is provided a first gate driver electrically coupled to the first and second MOSFETs and operable to apply a gate voltage to activate the first and second MOSFETs to engage the higher-ratio second primary sub-winding and a second gate driver electrically coupled to the third and fourth MOSFETs and operable to apply a gate voltage to activate the third and fourth MOSFETs to engage the lower-ratio first primary sub-winding.

In accordance with again a further feature of the invention, there are provided a first switch and a second switch, first and second switches being electrically coupled to the primary winding and operable to cause a current to flow in the primary winding.

In accordance with again an added feature of the invention, the first and second switches are MOSFETs.

In accordance with again an additional feature of the invention, there is provided at least one gate driver electrically coupled to the first and second switches and operable to apply a gate voltage to activate the first and second switches.

In accordance with still another feature of the invention, the at least one switching component is comprised of a relay or solid-state switch.

In accordance with still a further feature of the invention, the first switching component is comprised of a first MOSFET, the second switching component is comprised of a second MOSFET, and the third switching component is comprised of a third MOSFET.

In accordance with still an added feature of the invention, a first gate driver electrically coupled to the first MOSFET and operable to apply a gate voltage to activate the first MOSFET to engage the lower-ratio first primary sub-winding and a second gate driver electrically coupled to the second MOSFET and operable to apply a gate voltage to activate the second MOSFET to engage the higher-ratio second primary sub-winding.

In accordance with still an additional feature of the invention, the first MOSFET and the second MOSFET each have drains and the drains of the first and second MOSFETs are electrically coupled together and connected to the battery power source.

In accordance with another feature of the invention, the third MOSFET has a gate, a source, and a drain, the second MOSFET has a source and there is provided a pull-down driver electrically coupled to the gate of the third MOSFET, the source of the third MOSFET being connected to ground, the drain of the third MOSFET being electrically coupled to the source of the second MOSFET.

In accordance with a further feature of the invention, when the second MOSFET is activated and conducting current and the first and third MOSFETs are not activated such that they are not conducting current, the second primary sub-winding is engaged such that a current flows through the second primary sub-winding.

In accordance with an added feature of the invention, when the third MOSFET is activated and conducting current and the second MOSFET is not activated such that it is not conducting current, a current is induced in an opposite direction to have the current in the second primary sub-winding flow to ground through the third MOSFET causing a collapse of a magnetic field of the transformer.

In accordance with an additional feature of the invention, a current is induced in the first primary sub-winding by the collapse of the magnetic field of the transformer such that the current is conducted backwards through the first MOSFET and into the battery power source.

In accordance with yet another feature of the invention, when the first MOSFET is activated and conducting current and the second and third MOSFETs are not activated such that they are not conducting current, the entire primary winding is engaged such that a current flows through the primary winding.

In accordance with yet a further feature of the invention, when the third MOSFET is activated and conducting current and the first and second MOSFETs are not activated such that they are not conducting current, a current is induced in the primary winding in an opposite direction such that the current in the second primary sub-winding flows to ground through the third MOSFET causing a collapse of a magnetic field of the transformer.

In accordance with a concomitant feature of the invention, there is provided a fourth MOSFET electrically coupled to the source of the first MOSFET and connected to ground.

Additional advantages and other features characteristic of the present invention will be set forth in the detailed description that follows and may be apparent from the detailed description or may be learned by practice of exemplary embodiments of the invention. Still other advantages of the invention may be realized by any of the instrumentalities, methods, or combinations particularly pointed out in the claims. The construction and method of operation of the invention, however, together with additional objects and advantages thereof, will be best understood from the following description of specific embodiments when read in connection with the accompanying drawings.

Although the invention is illustrated and described herein as embodied in a battery-powered electrosurgical forceps with multi-turn selectable-ration transformer, it is, nevertheless, not intended to be limited to the details shown because various modifications and structural changes may be made therein without departing from the spirit of the invention and within the scope and range of equivalents of the claims.

Additionally, well-known elements of exemplary embodiments of the invention will not be described in detail or will be omitted so as not to obscure the relevant details of the invention.

BRIEF DESCRIPTION OF THE DRAWINGS

Advantages of embodiments of the present invention will be apparent from the following detailed description of the preferred embodiments thereof, which description should be considered in conjunction with the accompanying drawings in which.

DETAILED DESCRIPTION OF THE INVENTION

As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward. The figures of the drawings are not drawn to scale.

Before the present invention is disclosed and described, it is to be understood that the terminology used herein is for the purpose of describing particular embodiments only and is not intended to be limiting. The terms "a" or "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically.

Relational terms such as first and second, top and bottom, and the like may be used solely to distinguish one entity or action from another entity or action without necessarily requiring or implying any actual such relationship or order between such entities or actions. The terms "comprises," "comprising," or any other variation thereof are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

As used herein, the term "about" or "approximately" applies to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure.

Dual-Ratio Transformer Drive

Figure 1:
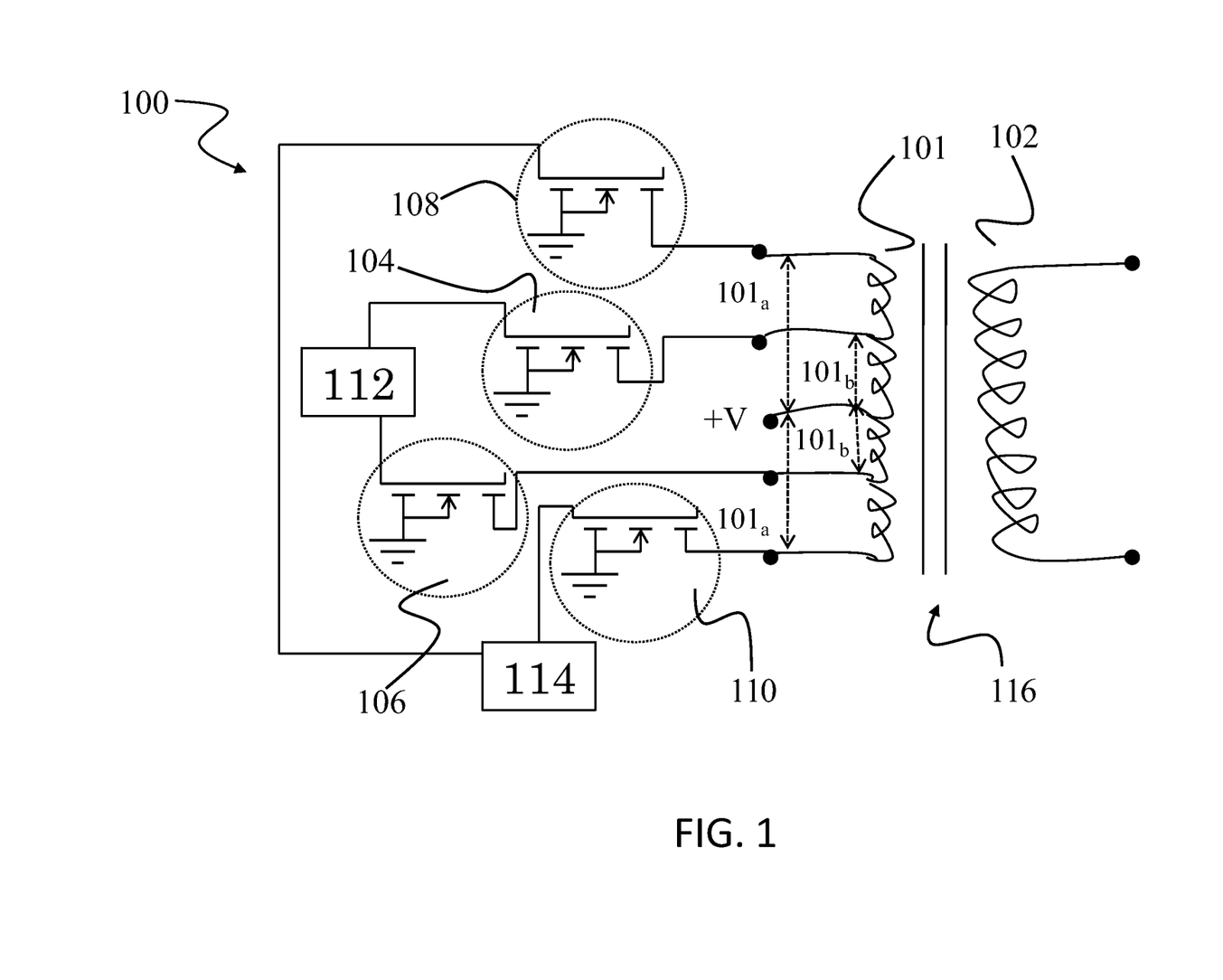
FIG. 1 is a fragmentary, schematic circuit diagram of a transformer with four switches controlling a multi-tapped primary winding for providing a selectable impedance electrocautery sealing and cutting surgical device in accordance with an exemplary embodiment of the present invention.

Referring now to the figures of the drawings in detail and first, particularly to FIG. 1 thereof, there is shown a schematic view of a first exemplary embodiment of the present invention where radio-frequency signal generating circuitry 100 is provided with a transformer 116 having a primary winding 101 and a secondary winding 102. The primary winding 101 includes a first primary sub-winding (hereinafter "PSW") $101_a$ and a second PSW $101_b$, each having a different number of turns. In this exemplary embodiment, PSW $101_a$ has more turns than PSW $101_b$. Also, PSWs $101_a$ and $101_b$ are not necessarily separate windings, and PSW $101_a$ may, instead, be tapped at an intermediate point along its turns to create PSW $101_b$.

Four MOSFETs 104, 106, 108, 110 are used in the embodiment of FIG. 1 to control the switching between the PSWs $101_a$ and $101_b$. In general terms, when a voltage is applied to the gate of any of the MOSFETS 104, 106, 108, 110, that MOSFET begins conducting current. Therefore, in accordance with the present invention, a voltage is applied to the MOSFET coupled to the particular winding of either PSW $101_a$ or $101_b$, in order to engage that particular winding.

To apply the gate voltage and to cause operation of the MOSFETs 104 and 106, a "High" gate driver 112 is used in this exemplary embodiment. Similarly, for operation of the MOSFETs 108 and 110, a "Low" gate driver 114 is used in this exemplary embodiment. If the High gate driver 112 is driven, i.e., the driver 112 applies a voltage to MOSFETs 104 and 106, the higher-ratio PSW 1016 is engaged. Likewise, if the Low gate driver 114 is driven, i.e., the driver 114 applies a voltage to MOSFETs 108 and 110, the lower-ratio PSW $101_a$ is engaged.

Advantageously, because the MOSFETs 104, 106, 108, 110 are located on the primary side of the transformer 116, low-voltage switching can take place and, therefore, low-voltage MOSFETs can be used, which reduces cost and improves reliability. It should be noted that the gate drivers 112 and 114 are represented in FIG. 1 only diagrammatically. This representation is intended to indicate that any device or circuit capable of applying a voltage to the MOSFETS can be used. Additionally, although the PSWs $101_a$ and $101_b$ are shown and described as being activated by the MOSFETs 104, 106, 108, 110, many other types of switches can be used for activating the PSWs $101_a$ and $101_b$ without departing from the spirit and scope of the present invention.

The impedance ratio of a transformer is equal to the square of the turns ratio. By providing multiple windings on the transformer 116, radio-frequency signal generating circuitry may be operated with a range of output impedances, depending upon which tap of a multi-tap primary winding is driven by the associated circuitry. Thus, because the internal impedance of a typical Li-ion battery pack is only about 0.8 Ohms, in order to achieve maximum power delivery at a load impedance of 3 Ohms, it is advantageous for the transformer 116 to have a secondary-to-primary impedance ratio of 3.0:0.8, or 3.75:1, which translates into a turns ratio of approximately 2:1. If, for example, the primary winding 101 has 10 turns and is tapped at 2 turns and the secondary winding 102 has 20 turns, a secondary-to-primary turns ratio of either 2:1 or 10:1 may be utilized from the single tapped transformer 116. If the power supply, e.g., battery "V", is 12 VDC, and is connected to the transformer's primary winding 101, the transformer's secondary winding 102 would produce approximately 24 or 240 Vrms, depending on which winding is utilized. Thus, in the high-current (low-impedance) mode of operation, a transformer with 10 primary turns and 20 secondary turns would be an appropriate choice. When driven with 12 VDC, the radio-frequency signal generating circuitry would produce 24 Vrms at 7.5 amps into a 3-Ohm load impedance.

Figure 2:
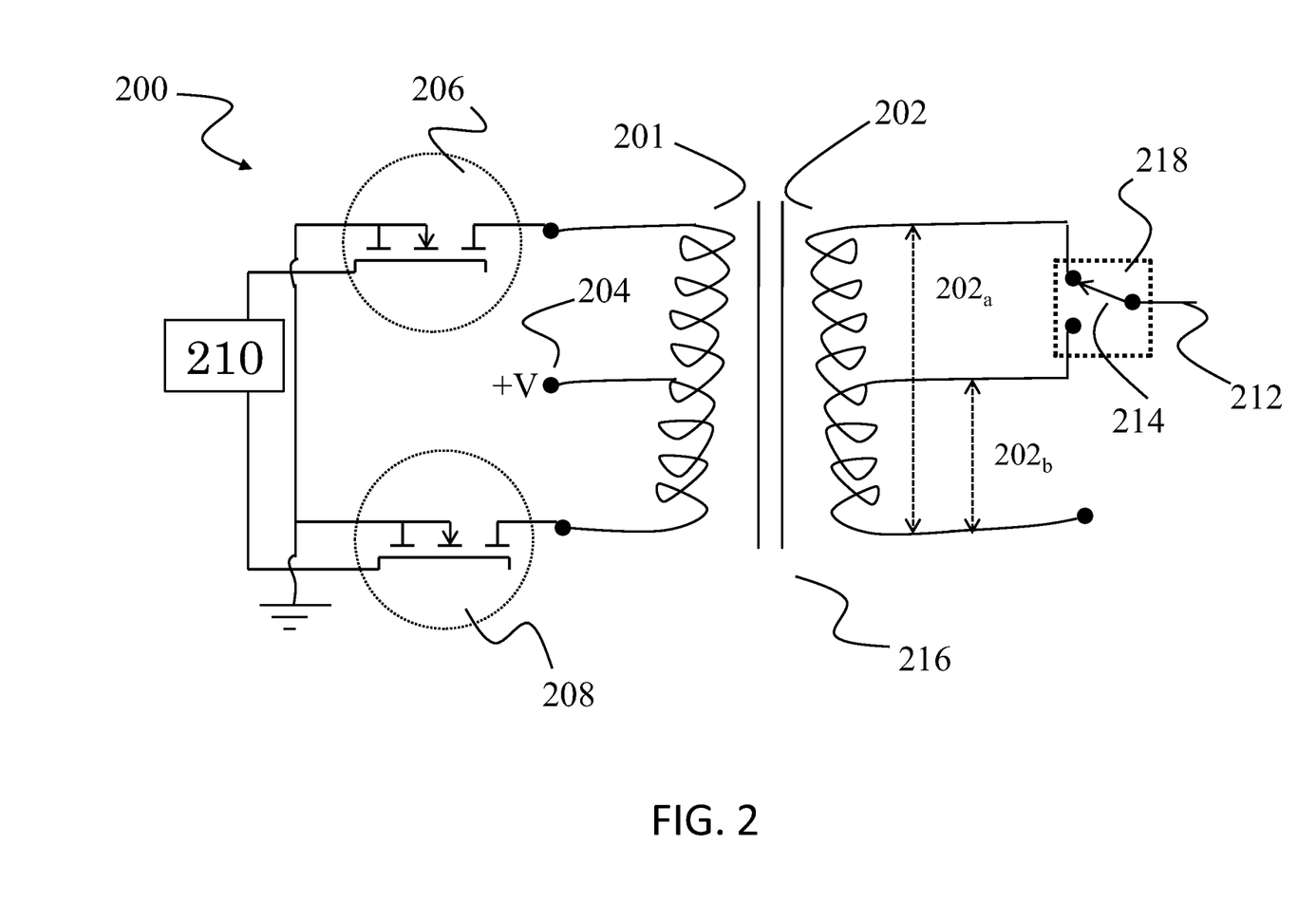
FIG. 2 is a fragmentary, schematic circuit diagram of a transformer with two switches controlling a primary winding and a switch controlling a tapped secondary winding for providing a selectable impedance electrocautery sealing and cutting surgical device in accordance with an exemplary embodiment of the present invention.

As the operation proceeds, and the load impedance increases to 100 Ohms, an impedance ratio of 100:0.8, or 125:1, becomes the appropriate choice, which would require a turns ratio of approximately 11:1. Therefore, the desired number of turns in the primary winding would be approximately 2 turns (only integer numbers of turns is practicable), resulting in a secondary-to-primary turns ratio of 20:2 (or 10:1) when coupled to the 20-turn secondary winding in this example. In this second mode of operation, the radio-frequency signal generating circuitry is capable of delivering 120 Vrms at 1.5 amps into a 100-Ohm load impedance. Thus, if supplied with 12 VDC, the radio-frequency signal generating circuitry could deliver either 24 Vrms at 7.5 amps (with all 10 turns of the primary winding in use) or 120 Vrms at up to 1.5 amps (with only 2 turns of the primary winding in use). Such a system advantageously achieves nearly optimum power delivery over the 3.0-Ohm to 100-Ohm range of impedance of the tissue being treated.

Secondary Switching FIG. 2 shows a second exemplary embodiment of the present invention where, unlike the transformer configuration of FIG. 1, switching takes place on the secondary winding 202 of the transformer 216. Here, the primary winding 201 is fed at point 204 by the power supply, e.g., battery "V". A pair of switches 206, 208, in this case MOSFETs, control current flow through the primary winding 201. A gate driver 210 activates the MOSFETs 206, 208 by applying voltage to the gates of the MOSFETs 206, 208, causing the MOSFETs 206, 208 to conduct current and allow the primary winding 201 to do the same.

The secondary winding 202 includes a first secondary sub-winding (hereinafter "SSW") $202_a$ and a second SSW $202_b$, each having a different number of turns. For purposes of the instant exemplary embodiment, SSW $202_a$ has more turns than SSW $202_b$. Also, SSWs $202_a$ and $202_b$ are not necessarily separate windings, and SSW $202_a$ may, instead, be tapped at a point along its turns to create SSW $202_b$.

A switch 218 selects between SSW $202_a$ and SSW $202_b$. The switch 218 can be, for instance, a relay or a solid-state switch. If the output is between a common lead 212 and the output lead 214 of the switch 218, the overall output voltage can be determined by the position of the switch 218, i.e., which SSW is selected. The transformer configuration of FIG. 2 is advantageous in that the primary is very simple, i.e., only two low-voltage MOSFETs are used. Further, the switch 218 can be switched during zero crossing points (i.e., low or zero voltage) of the output signal, thereby potentially extending the life of the switch 218. For instance, if the switch 218 is a relay, switching at zero crossing points (0 volts) will reduce stress on the contacts.

By providing multiple windings on the secondary 202 of the transformer 216, a radio-frequency signal generating circuitry may be operated with a range of output impedances, depending upon which tap of a multi-tap secondary 202 is driven by the associated circuitry. Again, the internal impedance of a typical Li-ion battery pack, e.g., "V", is only about 0.8 Ohms. In order to achieve maximum power delivery at a load impedance of 3 Ohms, it is advantageous for the transformer 216 to have a secondary-to-primary impedance ratio of 3.0:0.8, or 3.75:1, which translates to a turns ratio of approximately 2:1. If, for example, the primary winding 201 has 10 turns and the secondary winding 202 has 100 turns (202a) with a tap at 20 turns (202b), a secondary-to-primary turns ratio of either 1:10 or 1:2 may be utilized from the single tapped transformer 216. If the power supply, e.g., battery "V", is 12 VDC, and is connected to the transformer's primary winding 201, the transformer's secondary winding 202 would produce approximately 24 or 240 Vrms, depending on which winding is utilized. Thus, in the high current (low-impedance) mode of operation, a transformer 216 with 10 primary turns and 20 secondary turns would be an appropriate choice. When driven with 12 VDC in this mode, the radio-frequency signal generating circuitry would produce 24 Vrms at 7.5 amps into a 3-Ohm load impedance.

As the operation proceeds, and the load impedance increases to 100 Ohms, an impedance ratio of 100:0.8, or 125:1 becomes the appropriate choice, which would require a turns ratio of approximately 11:1. Therefore, the desired number of turns in the secondary winding would be approximately 100 turns (only integer numbers of turns is practicable), resulting in a secondary-to-primary turns ratio of 20:2 (or 10:1) when coupled to the 10-turn primary 201 in this example. In that mode of operation, the radio-frequency signal generating circuitry could deliver 120 Vrms at 1.5 amps into a 100-Ohm load. Thus, if supplied with 12 VDC, the radio-frequency signal generating circuitry could deliver either 24 Vrms at 7.5 amps (with only 20 turns of the secondary winding in use) or 120 Vrms at up to 1.5 amps (with all 100 turns of the secondary winding in use). Such a system would advantageously achieve nearly optimum power delivery over the 3.0-Ohm to 100-Ohm range of impedance of the tissue being treated.

Triple MOSFET

Figure 3:
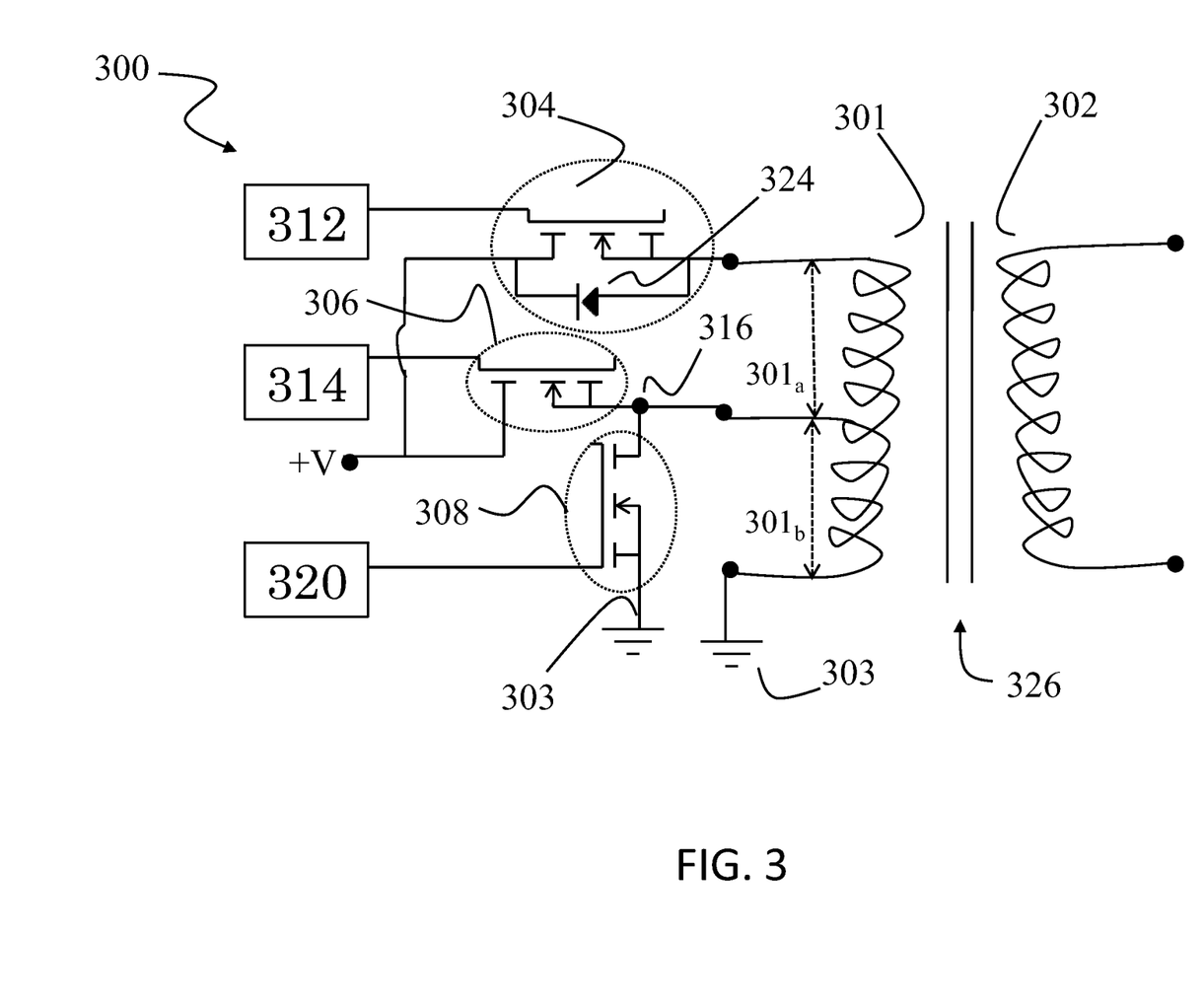
FIG. 3 is a fragmentary, schematic circuit diagram of a transformer with three switches controlling a multi-tapped primary winding for providing a selectable impedance electrocautery sealing and cutting surgical device in accordance with an exemplary embodiment of the present invention.

FIG. 3 provides a schematic view of yet another exemplary embodiment of the present invention where a transformer 326 is provided with a primary winding 301 and a secondary winding 302. The primary winding 301 includes a first primary sub-winding (hereinafter "PSW") $301_a$ and a second PSW $301_b$, each of which may have a different number of turns. PSWs $301_a$ and $301_b$ are not necessarily separate windings. Primary winding 301 may be tapped at a point along its turns to create PSW $301_a$ and PSW $301_b$. In this embodiment, both PSW $301_a$ and PSW $301_b$ are connected to ground 303 at one end thereof.

Three MOSFETs 304, 306, 308 are used in the embodiment of FIG. 3 to control the switching between the PSWs $301_a$ and $301_b$. As in the embodiment depicted in FIG. 1, a voltage applied to the gate of one of the MOSFETs 304, 306, 308 causes that MOSFET to switch on, i.e., conduct current. To apply the gate voltage and to cause operation of the first MOSFET 304, a "Low" gate driver 312 is used in this exemplary embodiment. Similarly, for operation of the second MOSFET 306, a "High" gate driver 314 is used in this exemplary embodiment. If the Low gate driver 312 is driven, i.e., driver 312 applies a voltage to the first MOSFET 304, the lower-ratio PSW $301_a$ is engaged. Likewise, if the High gate driver 314 is driven, i.e., driver 314 applies a voltage to MOSFET 306, the higher-ratio PSW $301_b$ is engaged.

The drains of the first MOSFET 304 and the second MOSFET 306 are coupled together and connected to a voltage source "V". Additionally, a further MOSFET 308 is connected between point 316 and ground 303 so that its source is connected to ground 303, its drain is connected to the source of the second MOSFET 306, and its gate is coupled to a pull-down driver 320.

Figure 4:
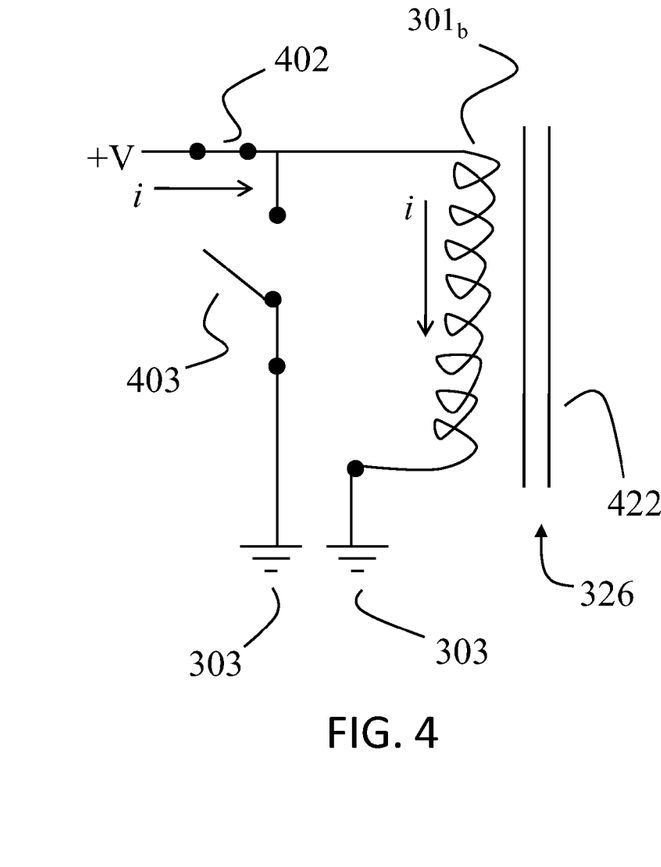
FIG. 4 is a fragmentary, schematic circuit diagram of the primary side of the transformer of FIG. 3 showing switching positions during a first one of the selectable impedance settings for the electrocautery sealing and cutting surgical device in accordance with an exemplary embodiment of the present invention.

The circuit configuration of FIG. 3 provides two main modes of operation. In the first mode, the second MOSFET 306 and the third MOSFET 308 alternate "on" modes with each other, forming a normal "totem-pole" drive through the PSW $301_b$, while the first MOSFET 304 remains "off." When the second MOSFET 306 is conducting current and the other two MOSFETs are off, current passes through the PSW $301_b$. This configuration is represented in FIG. 4, where diagrammatic switch symbols 402 and 403 represent second and third MOSFETs 306 and 308, respectively.

Figure 5:
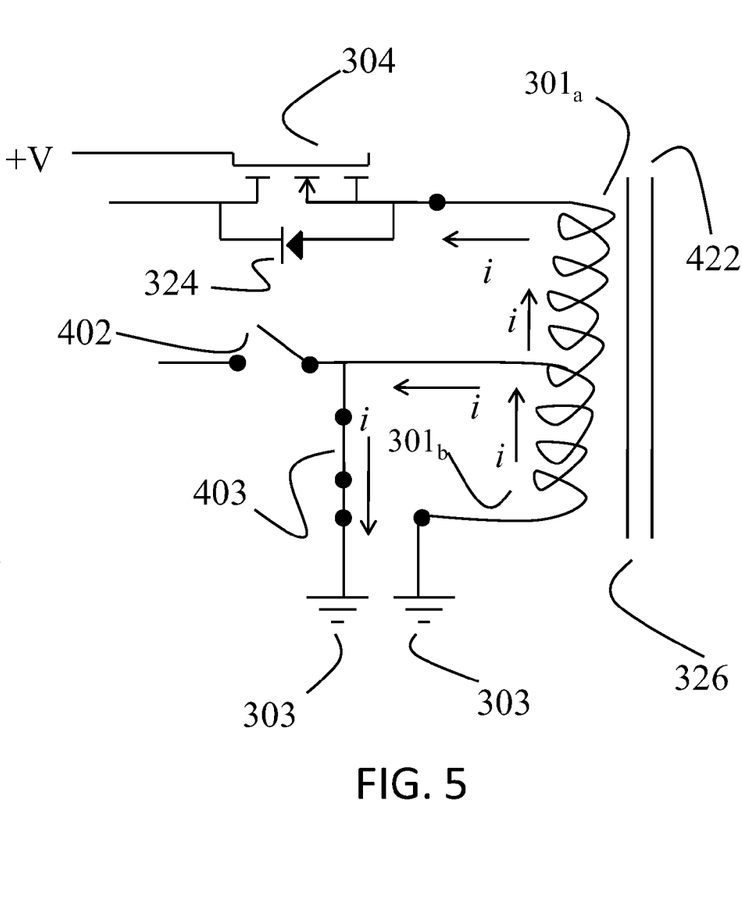
FIG. 5 is a fragmentary, schematic circuit diagram of the primary side of the transformer of FIG. 3 showing current flow during the switching phase from the first impedance setting to the second selectable impedance setting for the electrocautery sealing and cutting surgical device in accordance with an exemplary embodiment of the present invention.

As diagrammatically represented in FIG. 5, when the third MOSFET 308 turns on (switch 403) and the second MOSFET 306 turns off (switch 402), the magnetic flux stored in the core 422 of the transformer 326 collapses and induces current "i" in the opposite direction. Current in the lower portion of the primary winding, i.e., PSW $301_b$, easily flows to ground 303 through the third MOSFET 308 (switch 403). However, the collapsing magnetic field in the core also induces current in the upper portion of the primary, i.e., PSW $301_a$, which pushes a positive voltage spike upwards to the first MOSFET 304. Due to the "body diode" effect (a representative diode 324 is shown in the first MOSFET 304 in FIGS. 3 and 5), current is conducted backwards through the first MOSFET 304 and into the power supply "V". This return of power to the power supply "V" is referred to as "regeneration" and advantageously extends the life of the power supply charge.

Figure 6:
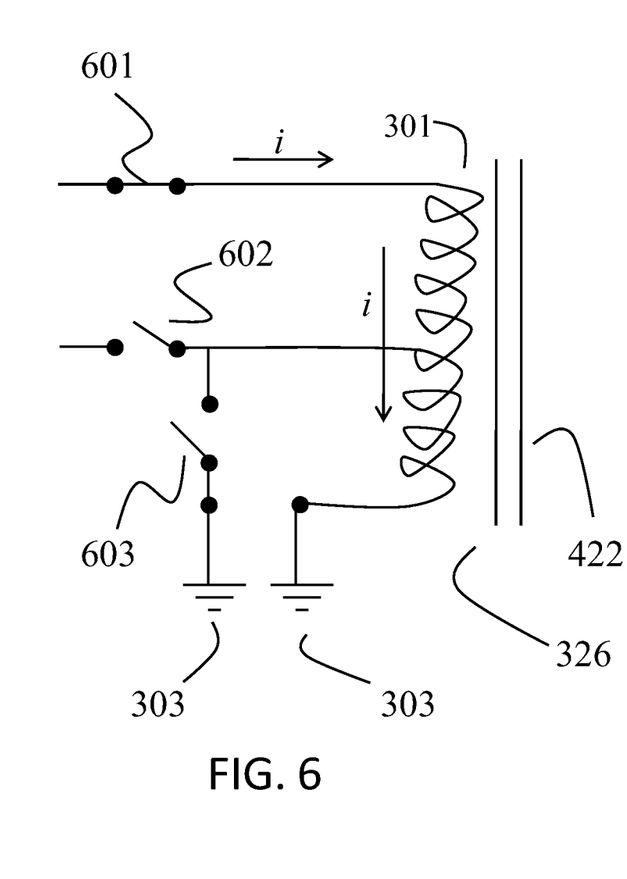
FIG. 6 is a fragmentary, schematic circuit diagram of the primary side of the transformer of FIG. 3 showing a second one of the selectable impedance settings for the electrocautery sealing and cutting surgical device in accordance with an exemplary embodiment of the present invention.

In a second mode of operation, the first MOSFET 304 alternates with the third MOSFET 308 forming a totem-pole drive into the lower portion of the primary winding 301, which will produce a higher turns ratio in the transformer 326. This second mode is shown in FIG. 6, where switches 601, 602, and 603 represent first, second, and third MOSFETs 304, 306, and 308, respectively. In this mode, when the first MOSFET 304 (switch 601) is conducting current and the second MOSFET 306 (switch 602) and third MOSFET 308 (switch 603) are off, the entire primary winding 301 is in use. In this mode, a current "i" flows through the first MOSFET 304, through the entire primary winding 301, and to ground 303.

Figure 7:
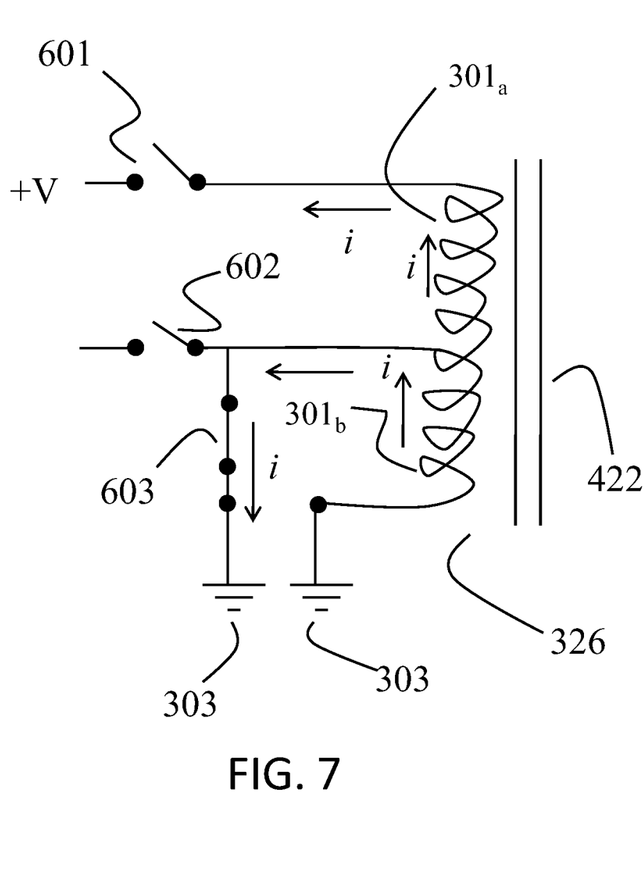
FIG. 7 is a fragmentary, schematic circuit diagram of the primary side of the transformer of FIG. 3 showing current flow during the switching phase from the second impedance setting to the first selectable impedance setting for the electrocautery sealing and cutting surgical device in accordance with an exemplary embodiment of the present invention.

When the first and third MOSFETs 304 and 308 change switching states, that is, the first MOSFET 304 (switch 601) stops conducting current, the third MOSFET 308 (switch 603) begins conducting current, and the second MOSFET 306 (switch 602) remains off, the magnetic flux within the core 422 of the transformer 326 collapses and induces a current in the opposite direction in the primary winding 301, which induced current is shown in FIG. 7. Current in the lower portion of the primary, PSW $301_b$, flows to ground through the third MOSFET 308 (switch 603) and the current being induced in the upper portion PSW $301_a$ of the primary winding 301 creates a voltage spike at the first MOSFET 304 (switch 601) and, as a result, through regeneration and the diode effect, returns to the power supply "V".

The circuit configuration shown in FIGS. 3 to 6 is advantageous in that all switching is performed on the primary side of the transformer and, thus, at low voltage. The invention, therefore, makes it possible to use low-voltage MOSFETs, which reduces cost and improves reliability. Further, the configuration facilitates instant High-Low mode shifting as there is no need to wait for zero crossings of signals before switching, as may be necessary on the higher-voltage secondary side. Additionally, only three MOSFETs are utilized in this circuit configuration. Again, although the PSWs $301_a$ and $301_b$ are shown and described as being activated by the MOSFETs 304, 306, 308, many other types of switches can be used for activating the PSWs $301_a$ and $301_b$ without departing from the spirit and scope of the present invention.

Quadruple MOSFET

Figure 8:
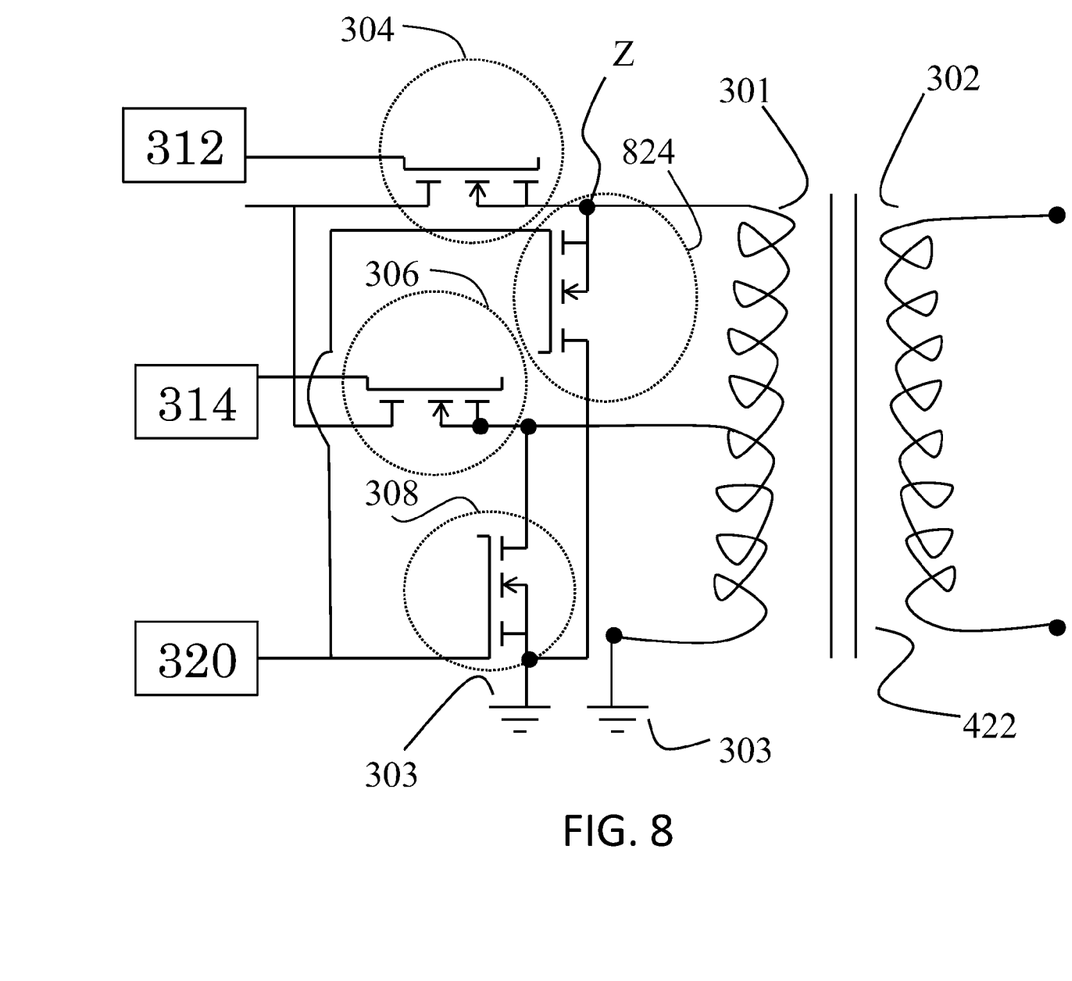
FIG. 8 is a fragmentary, schematic circuit diagram of a transformer with four switches controlling a multi-tapped primary winding for providing a selectable impedance electrocautery sealing and cutting surgical device in accordance with an exemplary embodiment of the present invention.

In yet another exemplary embodiment of the present invention, as shown in FIG. 8, a fourth MOSFET 824 is utilized. In this configuration, the fourth MOSFET 824 is connected between a point "Z" and ground 303, thereby forming a full totem-pole drive for the full primary winding 301. In this mode, both the third MOSFET 308 and the fourth MOSFET 824 are conducting current during the "grounding" portion of both the first and second modes discussed above. The fourth MOSFET 824 provides a low-resistance path to ground for current that is induced in the primary winding 301 by the collapsing magnetic field in the core 422. Providing this safe path to ground eliminates any potential damage that can occur to the first MOSFET 304 due to voltage spikes.

The circuit configuration shown in FIG. 8 is advantageous in that all switching is performed on the primary side of the transformer and, thus, at low voltage. Therefore, low-voltage MOSFETs can be used, which reduces cost and improves reliability. Further, the configuration facilitates instant High-Low mode shifting as there is no need to wait for zero crossings of signals before switching, as may be necessary on the higher-voltage secondary side of the transformer. Once again, although the PSWs $301_a$ and $301_b$ are shown and described as being activated by the MOSFETs 304, 306, 308, many other types of switches can be used for activating the PSWs $301_a$ and $301_b$ without departing from the spirit and scope of the present invention.

MOSFET Driver

The present invention provides source-load impedance matching between a battery-powered supply and a load of varying impedance. Manufacturers of integrated circuits for DC-DC converters have been developing more highly integrated control circuits in decreasingly smaller packages and with increasingly higher efficiencies, leading to lower electrical losses and a resulting reduced thermal output.

Figure 11:
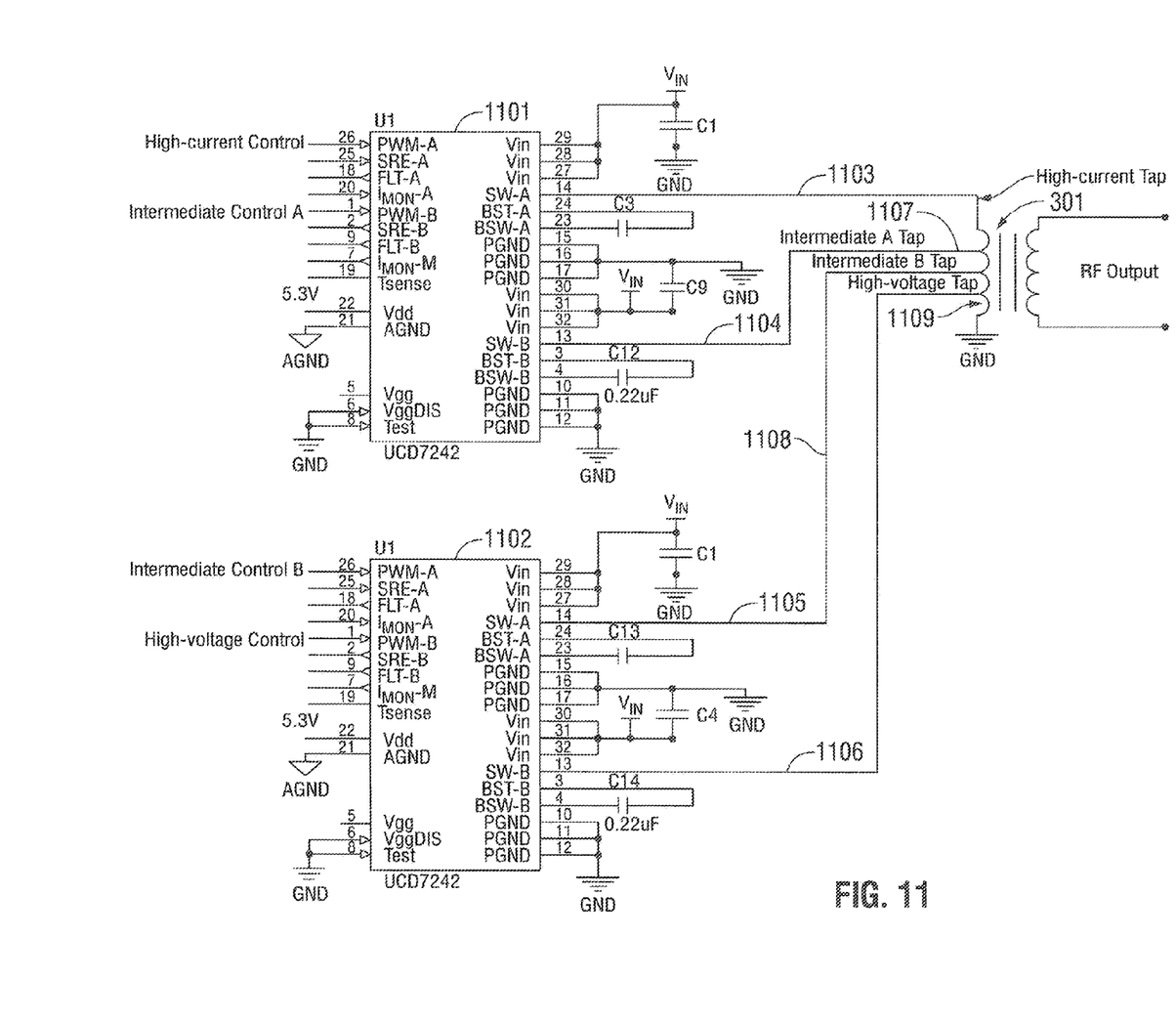
FIG. 11 is a fragmentary, schematic circuit diagram showing two DC-DC converters, such as the converter of FIG. 9, controlling the tapped primary winding of a transformer and providing a selectable impedance electrocautery sealing and cutting surgical device in accordance with an exemplary embodiment of the present invention.

These integrated circuits, such as, for example the UCD-7242 manufactured by TEXAS INSTRUMENTS, have enabled very small, highly efficient DC-DC converters. Typical application circuits employ one or more of these circuits as shown, for instance, in FIG. 9. The UCD-7242 incorporates control circuitry and the switching MOSFET devices for two separate DC-DC converters in a 6 mm-square package. These two sets of internal components may be combined into a two-phase converter to increase available load current and reduce voltage ripple. More than one such device may be incorporated into a single DC-DC converter; for example, as shown in FIG. 11, two UCD-7242 devices may be used to create a four-phase DC-DC converter with yet higher current capacity and a ripple current that is further reduced. Other manufacturers offer similar circuits, and more are in development to meet industry needs for small, efficient low-voltage DC supplies.

Figure 9:
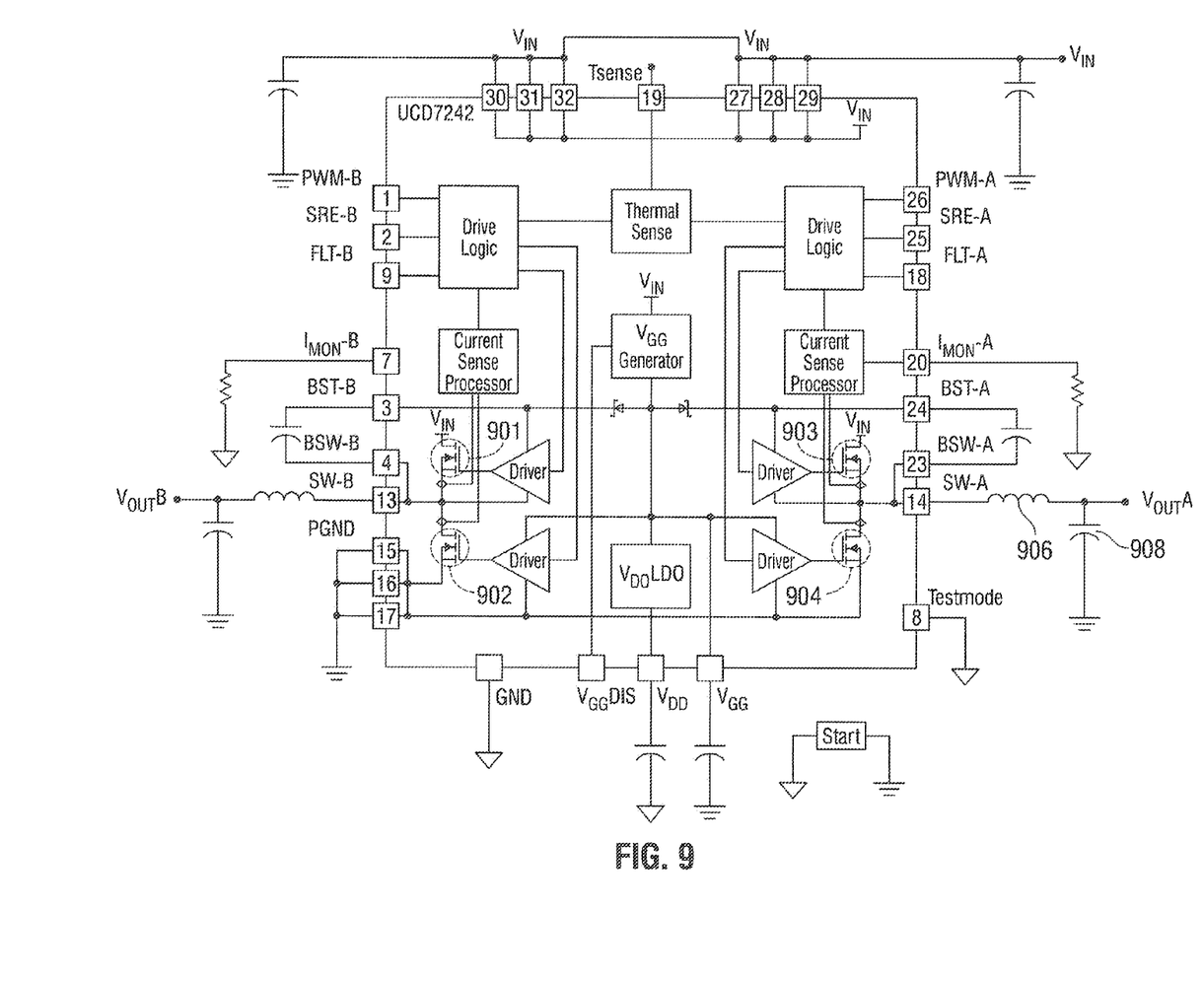
FIG. 9 is a schematic circuit diagram of a DC-DC converter in accordance with an exemplary embodiment of the present invention.

FIG. 9 illustrates equivalent internal circuitry of the UCD-7242. The two outputs, SW-A and SW-B, are each coupled to two MOSFET switches, where SW-A is coupled to switches 901 and 902 and SW-B is coupled to switches 903 and 904. The MOSFET switches allow switching of the load either to the input voltage, Vcc, or to power ground, PGND. In a standard buck-mode DC-DC converter using the "A" section of this circuit (right-hand side of FIG. 9), the common connection of these MOSFETs is connected through output SW-A to an external inductor 906 and capacitor 908 to smooth the DC output voltage. When the PWM-A input goes high, the high-side MOSFET is turned on, and when the PWM-A input goes low, the high-side MOSFET is turned off and (after a brief delay) the low-side MOSFET is turned on. This configuration is referred to as a "synchronous buck converter" because the low-side MOSFET that connects SW-A to ground is controlled to turn on when the high-side driver is switched off (the brief delay prevents short-circuiting Vcc to PGND). In the UCD-7242, as is common for many such control circuits, the low-side MOSFET may be enabled (its standard operation is to turn on when the high-side MOSFET is off) or it may be disabled, so that it never turns on, by the "Synchronous Rectifier Enable" connection SRE-A. Thus, it is possible to turn off both MOSFETs by making PWM-A low and SRE-A low. Such a condition effectively disconnects the SW-A output from either Vcc or power ground, leaving it floating (except for the action of the "internal body diodes" inherent with all MOSFET switches). For this reason, multiple sections (and multiple chips) may be operated in a parallel fashion to create multiphase DC-DC converters.

It has been discovered that, if the inductor 906 shown in FIG. 9 is, instead, replaced by the primary winding of a transformer, then an alternating voltage will be created across the secondary winding of the transformer. For the present invention, an alternating voltage is needed, which can be achieved by applying drive circuits such as the two MOSFETs 903 and 904 connected at SW-A to the primary winding of a transformer to create a high-voltage radio-frequency (RF) output for use in electrocautery surgical instruments.

In the quadruple MOSFET configuration of FIG. 3, a tapped primary winding 301 is driven with two pairs of MOSFET switches; 304 and 324 drive the full winding, and 306 and 308 drive the partial winding formed by the tap. In accordance with embodiments of the present invention, two sections of a controller, such as the UCD-7242 of FIG. 9, can be utilized to drive a tapped primary winding of a transformer. Such a configuration is shown in FIG. 10.

Figure 10:
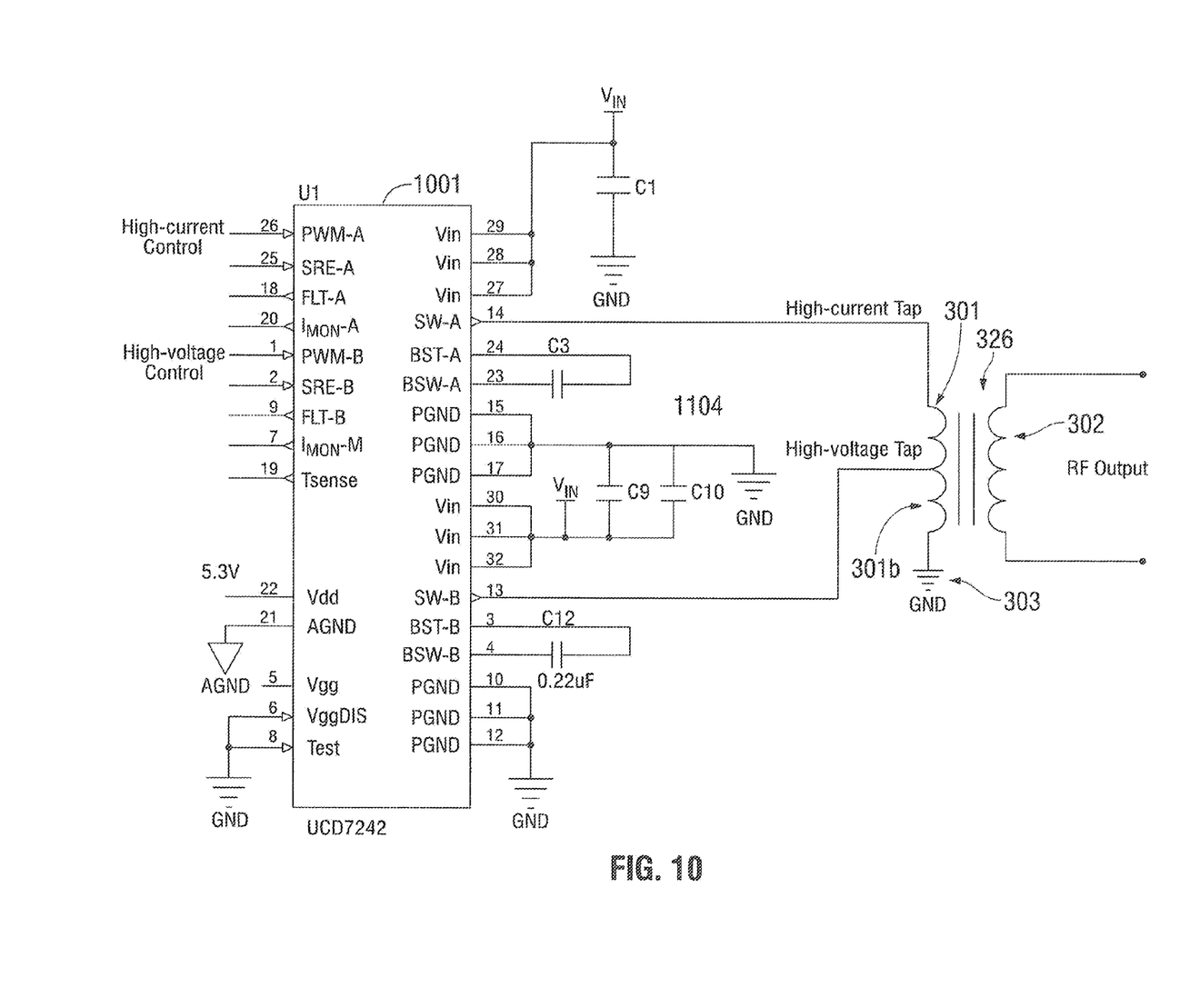
FIG. 10 is a fragmentary, schematic circuit diagram showing the DC-DC converter of FIG. 9 controlling the tapped primary winding of a transformer and providing a selectable impedance electrocautery sealing and cutting surgical device in accordance with an exemplary embodiment of the present invention.

In FIG. 10, the output SW-A of a controller chip 1001 is connected to the "High-current Tap" of the primary winding 301 of the transformer 326. The opposite end of the primary winding 301 is connected to ground 303. Therefore, the drive voltage at SW-A (pin 14) is applied to the full winding 301, resulting in the minimum voltage ratio with the secondary winding 302. Such a connection would supply the highest possible current because the turns ratio is as small as possible with the given primary winding 301. In a "high-current" operation, both MOSFET switches in Section "B" of the circuit (left side of FIG. 9) would be maintained in the off condition (PWM-A and SRE-A both held low). When high-voltage/low-current operation is desired, in order to efficiently couple power to a higher impedance load, Section B of the circuit would be brought into operation by applying a pulse-width modulated input to PWM-B and bringing SRE-B high. In this mode of operation, Section A would be disabled by holding both PWM-A and SRE-A low. Thus, under control of either a manual switch or a programmed microcontroller, either the full primary winding 301 or the smaller, tapped portion $301_b$ of the primary winding 301 can be brought into operation, resulting in either a high-current low-voltage or low-current high-voltage RF alternating-current output at the secondary winding 302.

FIG. 11 shows a further embodiment of the present invention where two UCD-7242 devices are used to create a four-phase DC-DC converter with high current capacity and reduced ripple current. In FIG. 11, two controller chips 1101 and 1102, with a total of four drive sections 1103, 1104, 1105, 1106, are used to drive a primary winding 301 with three taps 1107, 1108, 1109. Thus, the transformer may be operated with four different turns ratios, depending upon which of the four switching sections 1103, 1104, 1105, 1106 of the two UCD-7242 drive circuits is enabled. If section A (SW-A) of the upper chip 1101 is enabled, the highest-current lowest voltage RF output will be produced. If section B (SW-B) of the lower chip 1102 is enabled, the lowest-current highest voltage RF output will be produced.

As has been shown, an RF or a radio-frequency signal generating circuitry can be operated with a range of output impedances, depending upon which tap of a multi-tap primary winding 301 is driven by the associated circuitry. If, for example, an 8-turn primary winding 301—tapped at 2 turns, 4 turns, and 6 turns—is incorporated into a transformer with a secondary winding of 200 turns, a turns ratio of either 1:100, 1:50, 1:33, or 1:25 may be utilized from a single, tapped transformer. If the primary winding 301 is connected to a 12 VDC supply, then the transformer's secondary winding 302 would produce approximately 1200, 600, 396, or 300 Vrms, depending upon which of the taps is driven.

Therefore, in accordance with an embodiment of the present invention, four MOSFET-pair drive sections, as would be achieved by the use of two UCD-7242 chips (see FIG. 11), could provide four different impedance ratios, resulting in more efficient power delivery as the tissue load impedance changes from low to high during a cautery process.

The foregoing description and accompanying drawings illustrate the principles, preferred embodiments and modes of operation of the invention. However, the invention should not be construed as being limited to the particular embodiments discussed above. Additional variations of the embodiments discussed above will be appreciated by those skilled in the art as well as for applications, unrelated to inventory, that require encrypted identification of parts.

The above-described embodiments should be regarded as illustrative rather than restrictive. Accordingly, it should be appreciated that variations to those embodiments can be made by those skilled in the art without departing from the scope of the invention as defined by the following claims.

What is claimed is:

1. An electrocautery surgical device, comprising:
   a battery power source; and
   radio-frequency signal generating circuitry electrically coupled to the battery power source and operable to deliver power to an electrosurgical forceps, the radio-frequency signal generating circuitry comprising:
   a transformer having a primary winding and a secondary winding, the secondary winding being comprised of a first secondary sub-winding and a second secondary sub-winding;
   at least one switching component electrically coupled to the first and second secondary sub-windings and operable to switch between engaging the first secondary sub-winding and engaging the second secondary sub-winding such that a current induced by the primary winding flows through either the first secondary sub-winding or the second secondary sub-winding; and
   the first and second secondary sub-windings having a different number of turns such that the radio-frequency signal generating circuitry produces a different impedance value depending on which of the first or second secondary sub-windings is engaged.

2. The electrocautery surgical device according to claim 1, further comprising a first switch and a second switch, first and second switches being electrically coupled to the primary winding and operable to cause a current to flow in the primary winding.

3. The electrocautery surgical device according to claim 2, wherein the first and second switches are MOSFETs.

4. The electrocautery surgical device according to claim 3, further comprising at least one gate driver electrically coupled to the first and second switches and operable to apply a gate voltage to activate the first and second switches.

5. The electrocautery surgical device according to claim 1, wherein:
   the secondary winding has turns and is tapped at an intermediate point along the turns to create the first secondary sub-winding and the second secondary sub-winding.

6. The electrocautery surgical device according to claim 1, wherein the first secondary sub-winding and the second secondary sub-winding are separate windings electrically coupled to one another.

7. The electrocautery surgical device according to claim 1, wherein:

the second secondary sub-winding has a given number of turns; and the first secondary sub-winding has a number of turns greater than the given number of turns of the second secondary sub-winding.

8. The electrocautery surgical device according to claim 7, wherein:

the first secondary sub-winding has a given turns ratio; and the second secondary sub-winding has a turns ratio higher than the given turns ratio of the first secondary sub-winding.

9. The electrocautery surgical device according to claim 1, wherein the at least one switching component is comprised of a relay or solid-state switch.

* * * * *